(12) United States Patent
Moffitt et al.

(10) Patent No.: US 8,571,665 B2
(45) Date of Patent: Oct. 29, 2013

(54) HELICAL RADIAL SPACING OF CONTACTS ON A CYLINDRICAL LEAD

(75) Inventors: Michael Adam Moffitt, Valencia, CA (US); David Karl Lee Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 315 days.

(21) Appl. No.: 13/048,779

(22) Filed: Mar. 15, 2011

(65) Prior Publication Data

US 2011/0238129 A1    Sep. 29, 2011

Related U.S. Application Data

(60) Provisional application No. 61/316,691, filed on Mar. 23, 2010.

(51) Int. Cl.
*A61N 1/05* (2006.01)
(52) U.S. Cl.
USPC ............................ 607/45; 607/116; 600/378
(58) Field of Classification Search
USPC ......................................................... 607/116
See application file for complete search history.

(56) References Cited

U.S. PATENT DOCUMENTS

| | | | |
|---|---|---|---|
| 4,602,624 A | 7/1986 | Naples et al. | |
| 4,630,611 A | 12/1986 | King | |
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |

(Continued)

FOREIGN PATENT DOCUMENTS

| EP | 0580928 A1 | 2/1994 |
|---|---|---|
| EP | 0650694 B1 | 7/1998 |

(Continued)

OTHER PUBLICATIONS

U.S. Appl. No. 13/275,112, filed Oct. 17, 2011.

(Continued)

*Primary Examiner* — Kennedy Schaetzle
(74) *Attorney, Agent, or Firm* — Frommer Lawrence & Haug LLP; Bruce E. Black (57) ABSTRACT

A device for brain stimulation includes a lead having a longitudinal surface, a proximal end and a distal end; and a plurality of electrodes disposed along the longitudinal surface of the lead near the distal end of the lead. The plurality of electrodes includes at least four segmented electrodes having exposed surfaces where each exposed surface has a center point. The center points of the at least four segmented electrodes are disposed on a substantially helical path about the longitudinal surface of the lead.

20 Claims, 7 Drawing Sheets

(56) References Cited

U.S. PATENT DOCUMENTS

| | | | |
|---|---|---|---|
| 6,322,559 B1* | 11/2001 | Daulton et al. | 606/41 |
| 6,510,347 B2 | 1/2003 | Borkan | |
| 6,556,873 B1 | 4/2003 | Smits | |
| 6,564,078 B1 | 5/2003 | Marino et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,292,890 B2 | 11/2007 | Whitehurst et al. | |
| 7,319,904 B2* | 1/2008 | Cross et al. | 607/117 |
| 7,489,970 B2 | 2/2009 | Lee et al. | |
| 7,668,601 B2 | 2/2010 | Hegland et al. | |
| 7,715,923 B2* | 5/2010 | O'Brien et al. | 607/116 |
| 7,761,985 B2 | 7/2010 | Hegland et al. | |
| 7,809,446 B2 | 10/2010 | Meadows | |
| 7,840,188 B2 | 11/2010 | Kurokawa | |
| 7,856,707 B2 | 12/2010 | Cole | |
| 7,860,570 B2 | 12/2010 | Whitehurst et al. | |
| 7,949,409 B2* | 5/2011 | Bly et al. | 607/116 |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,225,504 B2 | 7/2012 | Dye et al. | |
| 8,295,944 B2 | 10/2012 | Howard et al. | |
| 2002/0156513 A1 | 10/2002 | Borkan | |
| 2002/0183817 A1 | 12/2002 | Van Venrooij et al. | |
| 2003/0109913 A1* | 6/2003 | Ketterl et al. | 607/116 |
| 2004/0098074 A1 | 5/2004 | Erickson et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0100495 A1* | 5/2006 | Santoianni et al. | 600/374 |
| 2006/0247697 A1 | 11/2006 | Sharma et al. | |
| 2007/0150007 A1 | 6/2007 | Anderson et al. | |
| 2007/0203546 A1 | 8/2007 | Stone et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2009/0171425 A1* | 7/2009 | Dahlberg | 607/127 |
| 2009/0204192 A1 | 8/2009 | Carlton et al. | |
| 2009/0204193 A1 | 8/2009 | Kokones et al. | |
| 2010/0036468 A1* | 2/2010 | Decre et al. | 607/116 |
| 2010/0076535 A1 | 3/2010 | Pianca et al. | |
| 2010/0082076 A1* | 4/2010 | Lee et al. | 607/17 |
| 2010/0094387 A1 | 4/2010 | Pianca et al. | |
| 2010/0268298 A1 | 10/2010 | Moffitt et al. | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |
| WO | 2009/128810 A1 | 10/2009 |
| WO | 2010/148376 A1 | 12/2010 |

OTHER PUBLICATIONS

U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
International Search Report and Written Opinion for International Patent Application No. PCT/US2011/028540 mailed May 19, 2011.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.
U.S. Appl. No. 13/906,776, filed May 31, 2013.

\* cited by examiner

HELICAL RADIAL SPACING OF CONTACTS ON A CYLINDRICAL LEAD

CROSS-REFERENCE TO RELATED APPLICATIONS

This application claims the benefit under 35 U.S.C. §119 (e) of U.S. Provisional Patent Application Ser. No. 61/316, 691 filed on Mar. 23, 2010, which is incorporated herein by reference.

FIELD

The invention is directed to devices and methods for brain stimulation including deep brain stimulation. In addition, the invention is directed to devices and method for brain stimulation using a lead having a plurality of electrodes disposed on a predefined substantially helical path about a substantially cylindrical lead.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near an end of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained. Furthermore, current methods often contain voids or dead spots, regions where stimulation cannot be performed, within the stimulation profile. These regions may require that the positioning of the lead be changed, and in some cases that the lead be removed and implanted in a different orientation.

BRIEF SUMMARY

One embodiment is a device for brain stimulation. The device includes a lead having a longitudinal surface, a proximal end and a distal end; and a plurality of electrodes disposed along the longitudinal surface of the lead near the distal end of the lead. The plurality of electrodes includes at least four segmented electrodes having exposed surfaces where each exposed surface has a center point. The at least four segmented electrodes are configured and arranged so that each of the center points are disposed at different longitudinal positions and at different radial positions about the longitudinal surface of the distal end of the lead.

Another embodiment is a device for brain stimulation. The device includes a lead having a longitudinal surface, a proximal end and a distal end; and a plurality of electrodes disposed along the longitudinal surface of the lead near the distal end of the lead. The plurality of electrodes includes at least four segmented electrodes having exposed surfaces where each exposed surface has a center point. The center points of the at least four segmented electrodes are disposed on a substantially helical path about the longitudinal surface of the lead.

Yet another embodiment is a method for brain stimulation that includes inserting a device into a cranium of a patient. The device includes a lead having a longitudinal surface, a proximal end and a distal end and a plurality of electrodes disposed along the longitudinal surface of the lead near the distal end of the lead. The plurality of electrodes include at least four segmented electrodes having center points, where the at least four segmented electrodes are disposed on a helical path about the longitudinal surface of the lead. The method also includes producing at least one of an anodic current or a cathodic current at the plurality of electrodes to stimulate a target neuron using the plurality of electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of electrodes disposed in a substantially helical path about a substantially cylindrical lead.

The lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending U.S. patent application Ser. No. 12/237,888 ("Leads With Non-Circular-Shaped Distal Ends For Brain Stimulation Systems and Methods of Making and Using"). Each of these references is incorporated herein by reference in its respective entirety.

Figure 1:
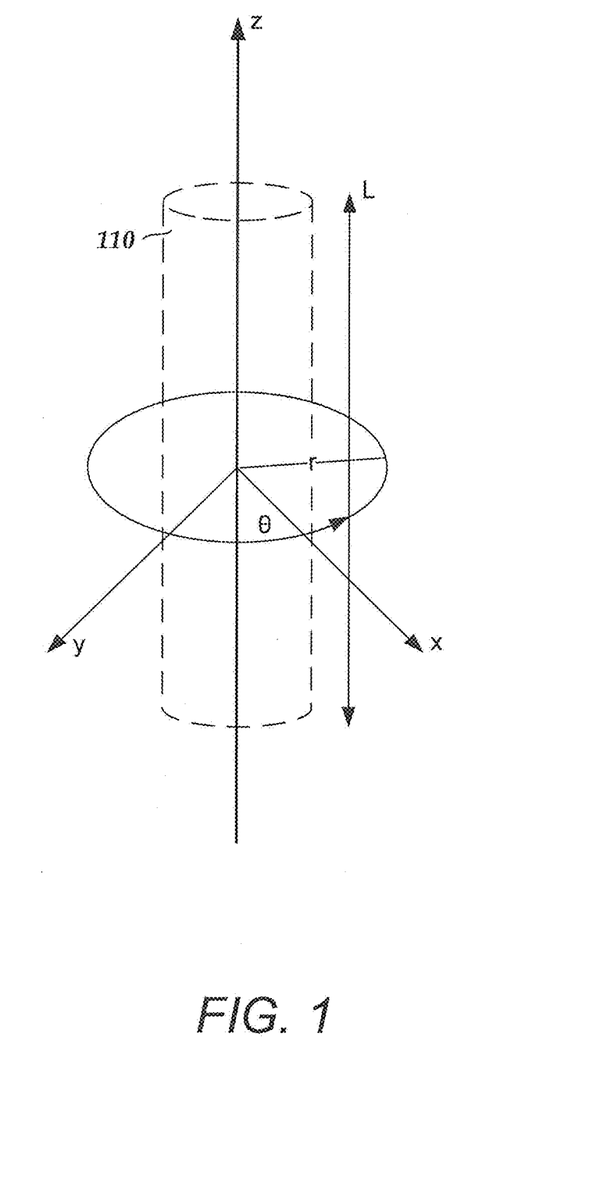
FIG. 1 is a schematic diagram of radial current steering along various electrode levels along the length of a lead, according to the invention.
Figure 2A:
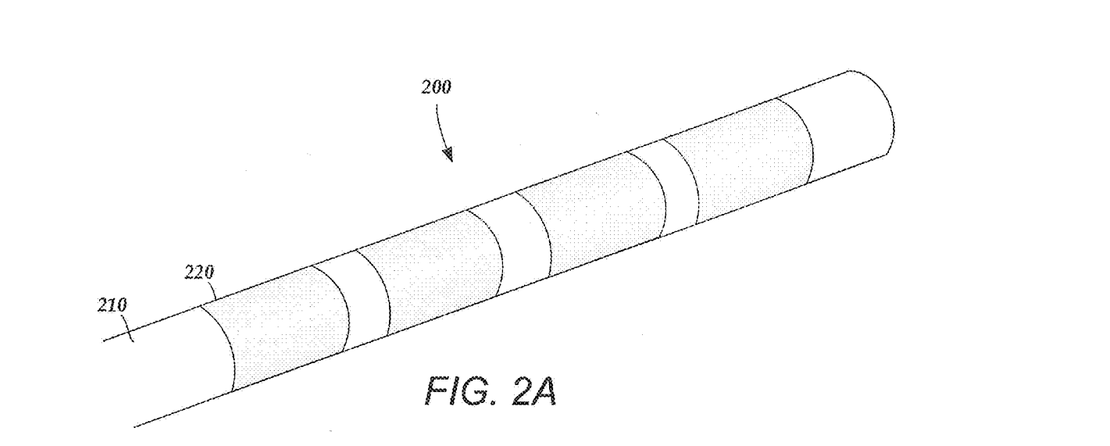
FIG. 2A is a schematic perspective view of a portion of a lead having a plurality of ring electrodes, according to the invention.
Figure 2B:
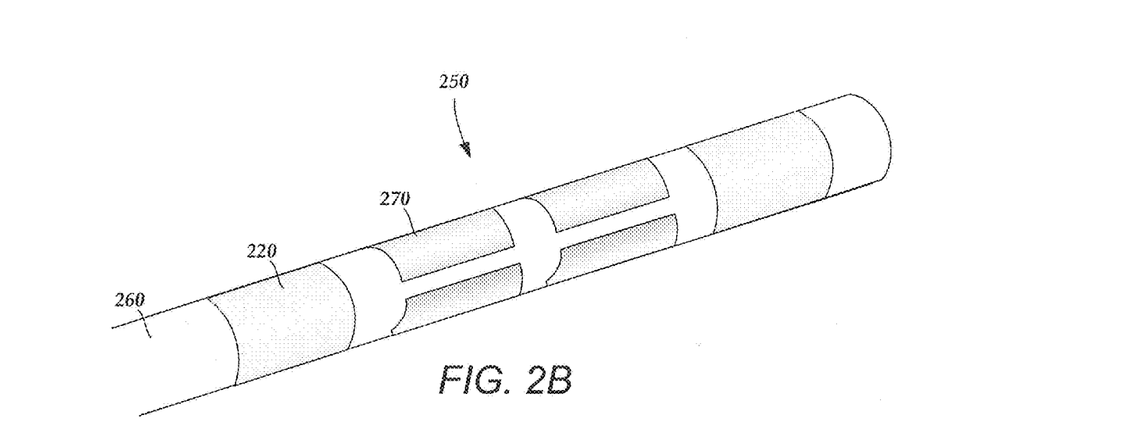
FIG. 2B is a schematic perspective view of a portion of a lead having a plurality of segmented electrodes and two ring electrodes, according to the invention.

FIG. 1 is a schematic diagram to illustrate radial current steering along various electrode levels along the length of a lead 110. Conventional lead configurations with ring electrodes 220, such as that shown in FIG. 2A, are only able to steer current along the length of the lead (the z-axis). Thus, as can be appreciated from FIG. 2A, the centroid of stimulation can be shifted at any level along the length of the lead (the z-axis in FIG. 1). In other embodiments, by placing a plurality of segmented electrode about the surface of the lead body, current may be steered in the x-axis, y-axis as well as the z-axis. As seen in FIG. 2B, multiple sets of segmented electrodes 270 may be disposed along the length of the lead 250 in addition to or instead of ring electrodes 220. The use of multiple sets of segmented electrodes may allow for three-dimensional current steering. In some embodiments, the radial distance, r, and the angle θ around the circumference of the lead body 260 may be dictated by the percentage of anodic current (recognizing that stimulation predominantly occurs near the cathode, although strong anodes may cause stimulation as well) introduced to each electrode. In at least some embodiments, the configuration of anodes and cathodes along the plurality of segmented electrodes allows the centroid of stimulation to be shifted to a variety of different locations along the lead body 260. It will be recognized that at least some embodiments, a separate anode or cathode (such as an anode or cathode provided on an implantable pulse generator coupled to the lead) may be used.

Thus, conventional radially segmented leads, such as those shown in FIG. 2B, may be helpful in improving the programmability of a deep brain stimulator because they can be controlled in multiple dimensions. By providing better control, stimulation of regions where therapy is undesirable can be minimized or avoided. In addition, control of the centroid of stimulation may be helpful in reducing the time needed to provide therapy.

Though radially segmented leads may provide better control of the area being stimulated, voids or dead spots, regions where selective stimulation cannot be achieved, may still be present in the stimulation profile. In order to stimulate a void or dead spot region, the lead may have to be maneuvered within the patient's body. In some instances, the lead may need to be removed and implanted a second time in order to achieve the proper stimulation. Thus, dead spots may often be the cause of ineffective therapy.

Figure 3A:
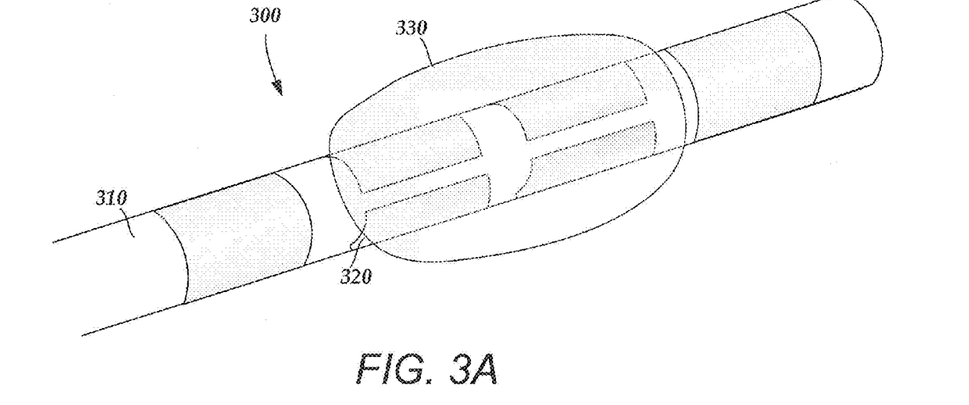
FIG. 3A is a schematic perspective view of a portion of a lead having a plurality of electrodes and illustrating one possible stimulation profile, according to the invention.

FIG. 3A is a schematic perspective view of radial selective stimulation using a portion of a lead having a plurality of segmented electrodes. The lead 300 includes multiple segmented electrodes 320 disposed on the lead body 310. The segmented electrodes 320 are capable of stimulating a region 330 around the lead 300. As can be appreciated from FIGS. 3A and 3B, the region of stimulation 330 may be controlled in all three axes as previously described above with reference to FIG. 1.

Figure 3B:
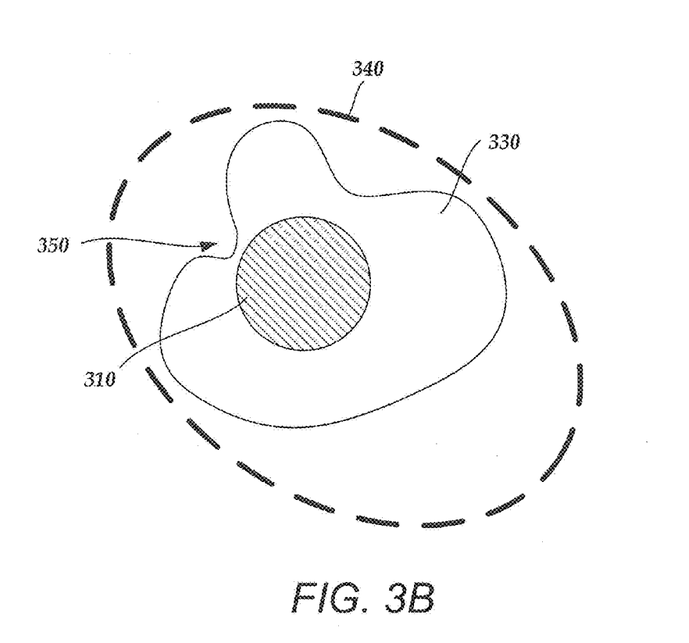
FIG. 3B is a schematic cross-sectional view of the portion of the lead of FIG. 3A and the associated stimulation profile, according to the invention.

FIG. 3B is a schematic cross-sectional of the portion of the lead 300 of FIG. 3A and the stimulation profile associated with the portion. As seen in FIG. 3B, the region of stimulation 330 is circumferentially disposed about the lead body 310. By controlling the amount of current directed to each segmented electrode, the stimulation profile can be modified as desired. For example, in one embodiment, the stimulation profile can be controlled so that no stimulation occurs outside of the target region 340. This type of control may be useful when a lead 300 has not been placed at the center of the target region 340. In such a situation, control of the stimulation profile may be useful to contain stimulation within the target.

As seen in FIG. 3B, though radially segmented electrodes are useful for controlling the profile of stimulation, voids or dead spots where stimulation cannot be achieved may still exist within the target region 340. These dead spots are usually located in regions between segmented electrodes. A dead spot 350 may result in ineffective stimulation and an increased time of treatment.

The number of electrodes and the position of the electrodes will dictate the possible stimulation profiles and the number of dead spots within those profiles. Positioning of the electrodes may be described by referring to the centers of the electrodes, hereinafter referred to as "center points." The center points may be located anywhere about the surface of the lead. In some embodiments, uniformly distributing the center points around a pre-defined longitudinal span of the lead will achieve a more desirable stimulation profile and selectivity profile.

Figure 4A:
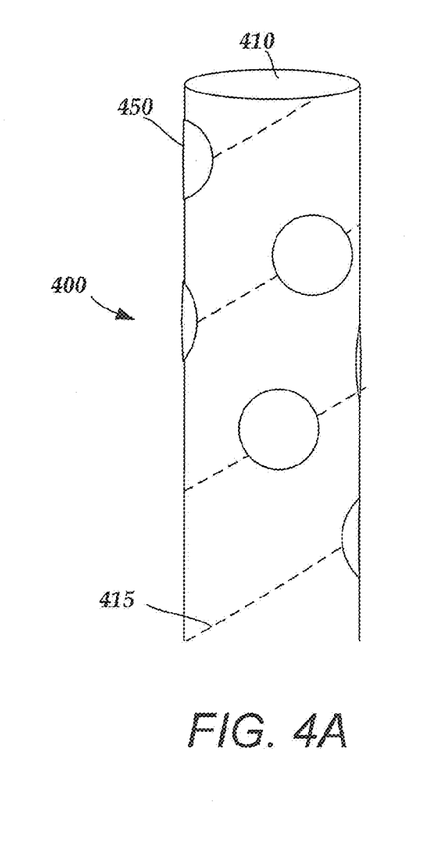
FIG. 4A is a schematic perspective view of one embodiment of a portion of a lead having a plurality of electrodes disposed on a helical path, according to the invention.

In some embodiments, the center points are disposed on a helical path about a cylindrical lead. FIG. 4A is a schematic view of one embodiment of a portion of a lead 400 having a plurality of electrodes disposed on a helical path 415 about the lead body 410. The center points of each of the electrodes 450 are shown to indicate the location of the electrode 450. FIG. 4A shows one embodiment, in which a lead 400 has eight electrodes 450, each having a center point, disposed along a helical path 415 with a longitudinal span of 6 mm.

As seen in FIG. 4A, the center points of the electrodes 450 may be disposed on a helical path 415 about the lead body 410. The arrangement of the electrodes may be described with reference to the number of electrodes disposed in one full turn of the helical path. In some embodiments, the electrodes may be arranged such that each full revolution of the helical path 415 includes two, three, four, five, six, seven, eight, ten, twelve, fourteen, or sixteen electrodes 450.

The helical path 415 may have any number of turns about the lead body 410. In some embodiments the helical path 415 forms one full turn about the circumference of the lead body 410. In some other embodiments, the helical path 415 forms two, three, four or five complete turns or revolutions about the lead body 410. It will be understood that the number of turns of the helical path 415 may be proportional to the number of electrodes 450 disposed on the lead 400 and it will also be understood that the helical path 415 may also include a partial turn, in addition to the one or more full turns. For example, in embodiments having eight electrodes 450, the helical path 415 may form two revolutions about the lead body 410 so that each revolution includes four electrodes 450. Any number of electrodes may be disposed on the lead 400. In some embodiments, on, two, three, four, five, six, seven, eight, nine, ten, twelve, fourteen or sixteen electrodes may be disposed on the lead 400. Similarly, in at least some embodiments, the number of revolutions formed by the helical path 415 may range from half a revolution to five full revolutions.

In some embodiments, the electrodes 450 are disposed about the longitudinal surface of the distal end of the lead 400 such that no two electrodes 450 are disposed at the same radial position. In some embodiments, the electrodes 450 are disposed along the longitudinal surface of the distal end, of the lead 400 such that no two electrodes 450 are disposed at the same longitudinal position. In some embodiments, such as embodiments having a helical path 415 of electrodes 450, the electrodes 450 may be disposed about the helical path 415 such that the electrodes 450 are disposed at different longitudinal positions and at different radial positions.

Figure 4B:
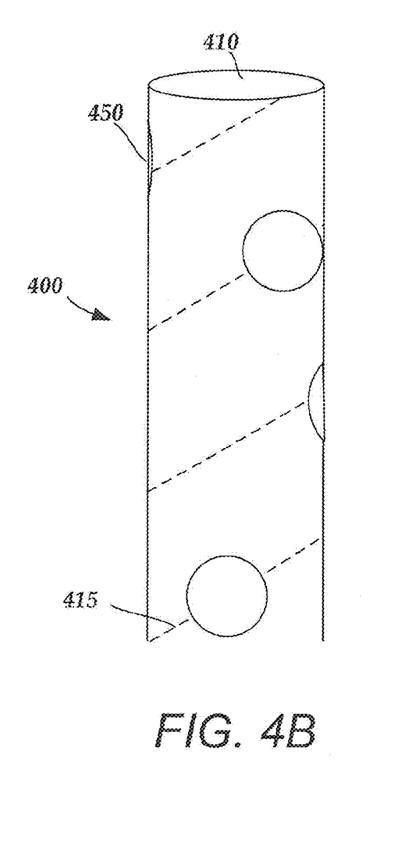
FIG. 4B is a schematic perspective view of another embodiment of a portion of a lead having a plurality of electrodes disposed on a helical path, according to the invention.

FIG. 4B is a schematic perspective view of another embodiment of a portion of a lead 400 having a plurality of electrodes disposed on a helical path 415. As can be appreciated from FIG. 4B, the helical path 415 of FIG. 4B is similar to the helical path 415 of FIG. 4A. However, the number of electrodes disposed on the lead 400 of FIG. 4B is less than the number of electrodes disposed on the lead 400 of FIG. 4A. Specifically, the lead 400 of FIG. 4B includes only half the number of electrodes disposed on the lead 400 of FIG. 4A. Thus, by including fewer electrodes 450 along the helical path 415, a different stimulation profile may be achieved. It will be appreciated that the distance between center points of electrodes 450 in FIG. 4B is twice the distance between center points of electrodes 450 in FIG. 4A along the helical paths 415.

Figure 4C:
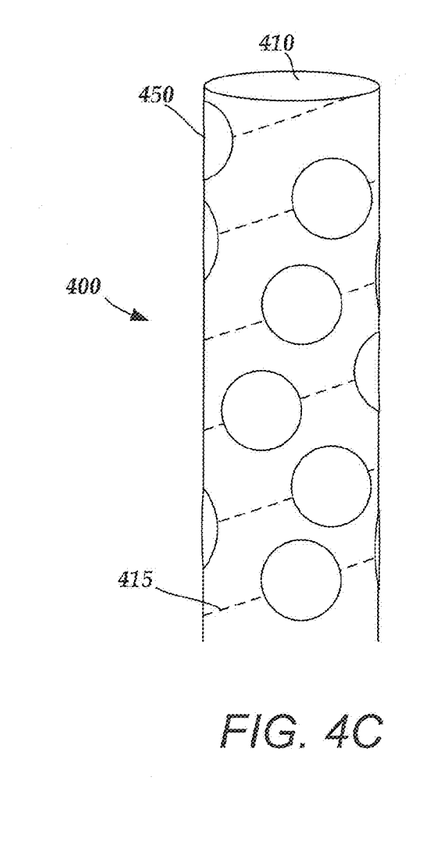
FIG. 4C is a schematic perspective view of a third embodiment of a portion of a lead having a plurality of electrodes disposed on a helical path, according to the invention.

In at least some other embodiments, the helical path 415 itself may also be modified to achieve a different stimulation profile. FIG. 4C is a schematic perspective view of a third embodiment of a portion of a lead 400 having a plurality of electrodes 450 disposed on a helical path 415. As seen in FIG. 4C, the helical path 415 includes more turns along a given length of the lead body 400 than the helical paths 415 of FIGS. 4A and 4B. With a predefined helical path 415, any number of electrodes 450 may be disposed along the helical path 415 as desired.

Thus, in some embodiments, the spacing of the electrodes 450 may be adjusted by changing the helix angle, defined as the angle between the helical path 415 and an axial line of the lead 400. In some embodiments, the helix angle is between 5 and 90 degrees. Thus, spacing of the electrodes 450 may be adjusted by choosing the appropriate helix angle, the number of electrodes, the number of revolutions desired or any combination thereof. Instead of choosing the helix angle, the longitudinal span of the helical path 415 and the number of revolutions may be chosen to obtain the helical path 415. For example, in some embodiments, the longitudinal span of the helical path 415 is between 3 mm and 15 mm. In some embodiments the longitudinal span is no more than 15 mm, 20 mm, 25 mm, 30 mm, or 40 mm. In some embodiments, the longitudinal span is at least 1 mm, 2 mm, 3 mm, 5 mm, or 10 mm. By choosing the longitudinal span and the number of revolutions of the helical path 415, the helical path 415 may be defined and the electrodes may be distributed.

In some embodiments, the electrodes 450 are uniformly distributed about the helical path 415 such that each center point of the electrode 450 is the same distance from the center point of the nearest neighboring electrode 450 along the helical path 415. For example, the location of the electrodes 450 may be chosen such that the distance between the adjacent center points of electrodes 450 along the helical path 415 are 2 to 4 mms apart (e.g. 2 to 2.6 mm apart). In at least some embodiments, the helical path 415 itself is chosen such that the electrodes 450 are uniformly distributed about the surface of the lead so that each electrode 450 is the same distance away from the nearest four electrodes 450. For example, a lead 400 may be formed wherein the center point of each electrode 450 is 2.43 mm away from the center points of the nearest four electrodes 450. By reducing the distance between electrodes 450, the number of voids or dead spots may be reduced within the stimulation profile.

Alternatively, the spacing between electrodes may be defined by the radial angle between them about the lead body. In some embodiments, the radial angle between adjacent center points is the same for each of the electrodes. For example, the radial angle between adjacent center points along the helical path may be between 10 and 270 degrees. In some embodiments, the radial angle between adjacent electrodes along the helical path is at least 30 degrees. In at least some other embodiments, the radial angular separation between adjacent center points along the helical path is at least 15 degrees, at least 30 degrees, at least 45 degrees, at least 60 degrees, at least 72 degrees, at least 90 degrees, at least 120 degrees, or 180 degrees.

In some embodiments, the electrodes may also be arranged about the longitudinal surface of the lead such that the sum of the distances between the center points of the electrodes is minimized. For example, in some embodiments a longitudinal span is first chosen. This longitudinal span defines the length of the helical path about which the electrodes will be disposed. Next, a cost function may be defined as the maximization of the minimum distance from any center point to any other center point. By evaluating the cost function, a resulting helical path may be obtained and the electrodes may be disposed on the path as desired.

Regardless of the parameter or the method used to locate the electrodes, by uniformly distributing the center points about the lead, the probability of being able to stimulate a given target point, without stimulating undesired points, is increased, and fewer adjustments may be made to the location of the lead after implantation. That is, the ability to selectively stimulate is increased.

Figure 5:
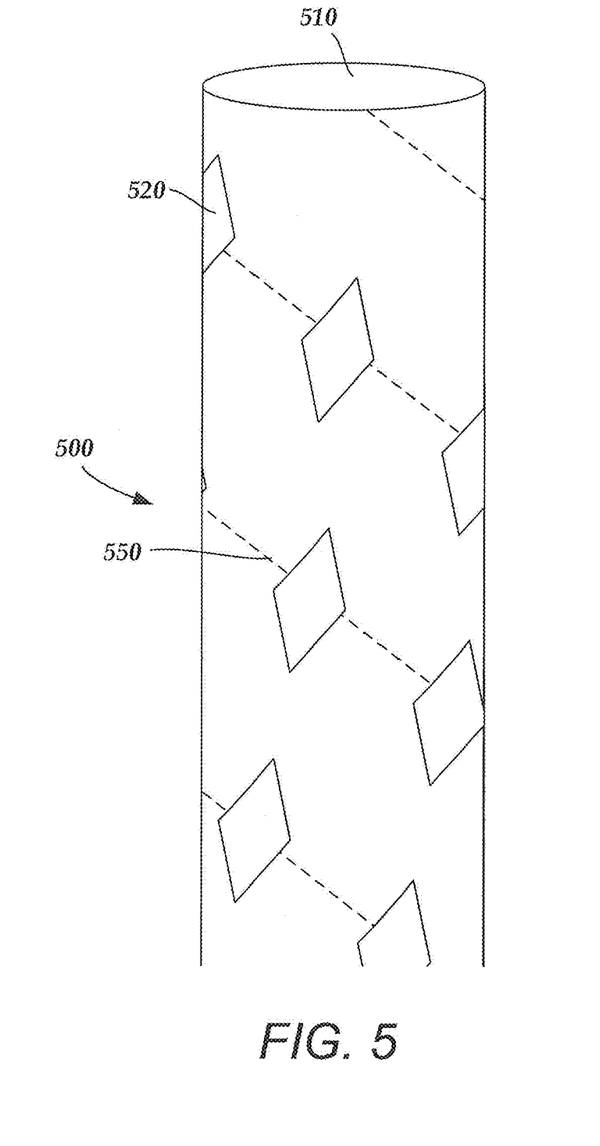
FIG. 5 is a schematic view of one embodiment of a portion of a lead having a plurality of diamond-shaped electrodes disposed on a helical path, according to the invention.

FIG. 5 is a schematic view of one embodiment of a portion of a lead having diamond-shaped segmented electrodes disposed on a helical path. Similarly to FIGS. 4A, 4B, and 4C, FIG. 5 shows a lead 500 having a plurality of electrodes 520 disposed on a helical path 550 about the lead body 510. The lead 500 includes electrodes (with two electrodes disposed on the back portion), although any number of electrodes may be disposed on the lead 500. The electrodes of FIG. 5 are disposed on the lead body 510 about a helical path 550 having a longitudinal span of 7.5 mm. Because the number of revolutions is the same as in FIG. 4, and the longitudinal span is increased, the helical path of FIG. 5 will have a greater helix angle, resulting in more spacing between the electrodes 520.

The electrodes can have any suitable shape and size. The electrodes may have the same shape or may have different shapes. The cross-sectional shape of the electrode may also vary. In some embodiments, as in FIG. 5, the electrodes 520 are diamond-shaped. In at least some other embodiments, the electrodes may have a cross-section that is a circle (see, e.g., FIGS. 4A, 4B, 4C, and 6), an oval, a rectangle, a square, or a triangle. Furthermore, it is possible to create a lead having multiple electrodes of different shapes. For example, a single lead may have both circular electrodes and diamond-shaped electrodes. The electrodes may be arranged in any desired configuration. For example, in some embodiments, the electrodes alternate between a first shape and a second shape.

Figure 6:
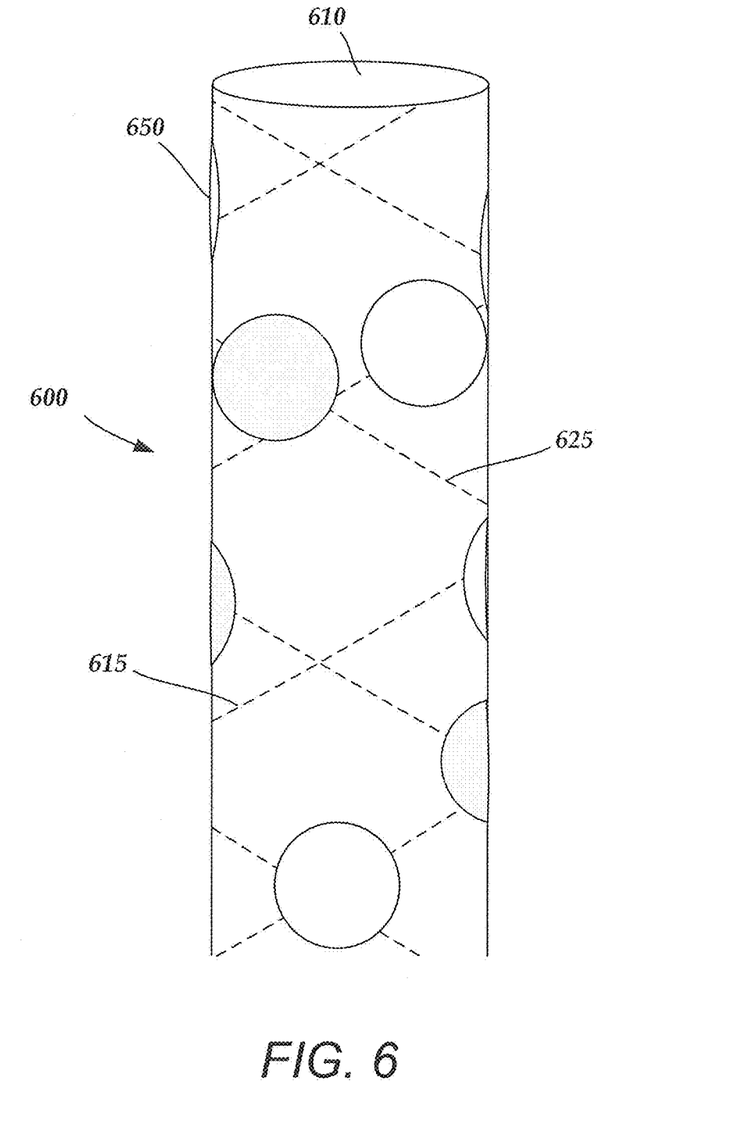
FIG. 6 is a schematic perspective view of a portion of a lead having a plurality of electrodes disposed on two helical paths, according to the invention.

FIG. 6 is a schematic perspective view of a portion of a lead having a plurality of electrodes disposed on two helical paths. This embodiment may be referred to as a "double helix" arrangement. In this embodiment, a first helical path 615 is defined along the circumference of the lead body 610. A first set of electrodes 650 is disposed on the first helical path 615. A second helical path 625 may then be defined along the circumference of the lead body 610. A second set of electrodes 650 may then be disposed on the second helical path 650.

As seen in FIG. 6, in some embodiments, the second helical path 625 may be defined to rotate in a direction opposite of the first helical path 615. For example, the orientation of the first helical path 615 may be defined such that the helical path rotates counterclockwise from the proximal end of the lead body 610 to the distal end of the lead body 610. The second helical path 625 may then be defined to rotate clockwise from the proximal end of the lead body 610 to the distal end of the lead body 610. In at least some other embodiments, the first helical path 615 and the second helical path 625 may be defined to rotate in the same direction.

In some embodiments, the first helical path 615 and second helical path 625 may be congruent. Alternatively, the first helical path 615 and the second helical path 625 may include a different numbers of turns, different helix angles, or they may span different lengths of the lead body 610. Additionally, the number of electrodes 650 disposed on the first helical path 615 and the second helical path 625 may be different. The distance between center points of electrodes 650 along the helical paths may also be different for the two paths.

In some embodiments, the shape of the electrodes disposed along the two helical paths is different. For example, the electrodes on the first helical path 615 may be circular, while the electrodes disposed on the second helical path 625 are diamond-shaped as seen in FIG. 5. Each helical path may also include two, three, or more shapes of electrodes.

The two helical paths may also be configured so as to stimulate the target tissues differently. For example, the set of electrodes 650 disposed on the first helical path 615 may be configured to stimulate the tissue at a first frequency, while the second set of electrodes 650 disposed on the second helical path 625 stimulates at a second frequency. It will be understood that any parameter of the stimulation profile may be modified. In some embodiments, the first helical path 615 and the second helical path 625 stimulate at different magnitudes, durations, or any combination thereof. In another embodiment, the set of electrodes 650 disposed on the first helical path 615 may be stimulating electrodes and the second set of electrodes 650 disposed on the second helical path 625 may be recording electrodes. The size and shape of these electrodes may be the same or different.

In this manner, different stimulation profiles may be achieved to treat the target tissue. For example, the first and second sets of electrodes 650 may be activated in an alternating manner. Alternatively, the two sets of electrodes 650 may both be activated simultaneously. In embodiments where each electrode is coupled to a separate or designated conductor, electrodes on only one side of the lead 610 may be activated.

Figure 7:
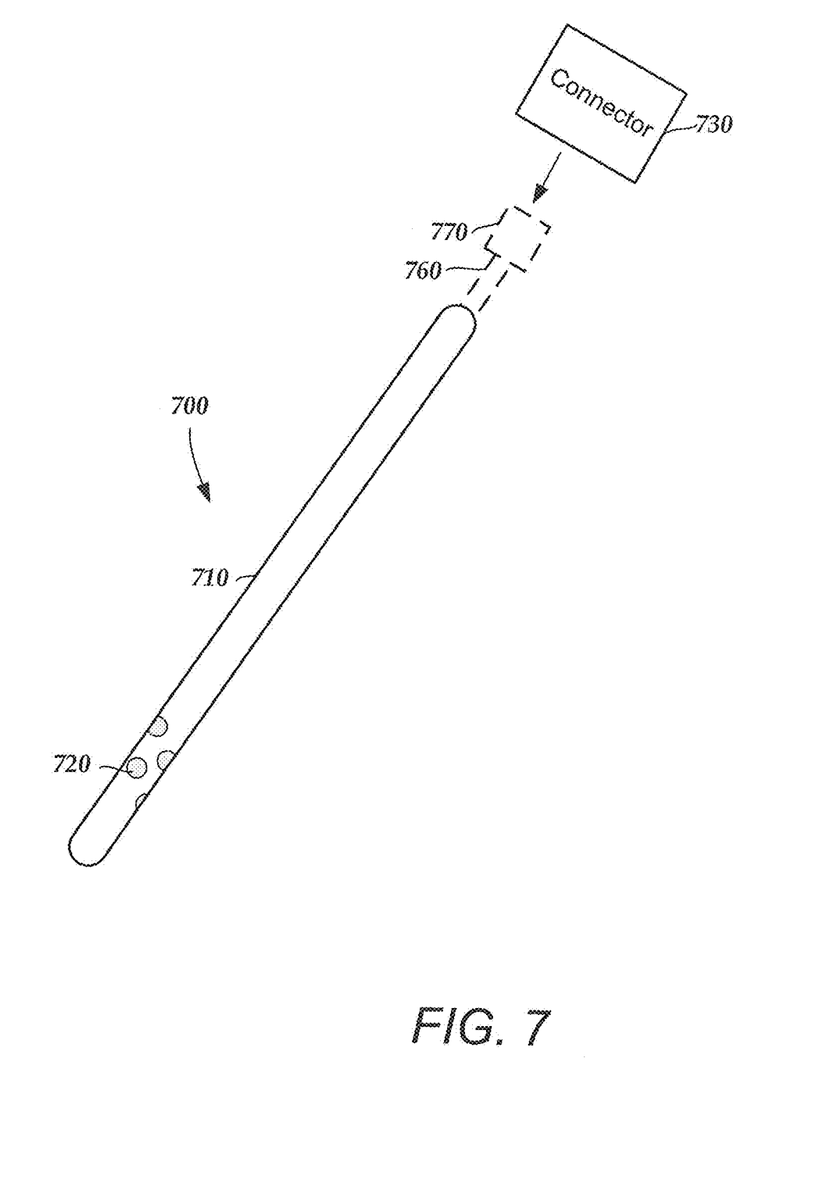
FIG. 7 is a schematic side view of one embodiment of a lead and a stylet, according to the invention.

FIG. 7 illustrates one embodiment of a device 700 for brain stimulation. The device includes a lead 710, a plurality of electrodes 720 helically disposed about the lead body 710, a connector 730 for connection of the electrodes to a control unit, and a stylet 760 for assisting in insertion and positioning of the lead in the patient's brain. The stylet 760 can be made of a rigid material. Examples of suitable materials include tungsten, stainless steel, or plastic. The stylet 760 may have a handle 770 to assist insertion into the lead, as well as rotation of the stylet and lead. The connector 730 fits over the proximal end of the lead 710, preferably after removal of the stylet 760.

In one example of operation, access to the desired position in the brain can be accomplished by drilling a hole in the patient's skull or cranium with a cranial drill (commonly referred to as a burr), and coagulating and incising the dura mater, or brain covering. The lead 710 can be inserted into the cranium and brain tissue with the assistance of the stylet 760. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

It will be understood that the lead 710 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Though the following description discusses stimulation electrodes, it will be understood that all configurations of the stimulation electrodes discussed may be utilized in arranging recording electrodes as well.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle or other physiologic parameter or subjective patient response or any combination thereof and provide feedback.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for deep brain stimulation, comprising:
    a non-bifurcated lead having a longitudinal surface, a proximal end and a distal end; and
    a plurality of electrodes disposed along the longitudinal surface of the lead near the distal end of the lead, the plurality of electrodes comprising at least four segmented electrodes having exposed surfaces, each exposed surface having a center point, wherein all of the segmented electrodes of the device are arranged in either one single helix or one double helix and each electrode is separately activatable;
    wherein the at least four segmented electrodes are configured and arranged so that each of the center points are disposed at different longitudinal positions and at different radial positions about the longitudinal surface of the distal end of the lead.

2. The device of claim 1, wherein each of the center points of the at least four segmented electrodes are uniformly distributed about a portion of the longitudinal surface of the lead.

3. The device of claim 1, wherein each of the center points of the at least four segmented electrodes are disposed radially 72 degrees apart from a nearest one of the segmented electrodes.

4. The device of claim 1, wherein each of the center points of the at least four segmented electrodes are disposed radially 90 degrees apart from a nearest one of the segmented electrodes.

5. The device of claim 1, wherein adjacent center points of the at least four segmented electrodes are disposed radially 120 degrees apart from a nearest one of the segmented electrodes.

6. The device of claim 5, wherein the center point of each of the segmented electrodes is equidistant from the center points of the four closest segmented electrodes to that segmented electrode.

7. The device of claim 5, wherein the center point of each of the segmented electrodes ranges from about 2 to 2.6 mm from the center points of the four closest segmented electrodes.

8. The device of claim 1, wherein the plurality of electrodes comprises eight segmented electrodes.

9. The device of claim 1, wherein the segmented electrodes are diamond shaped.

10. The device of claim 1, wherein the center points are arranged about the longitudinal surface of the lead such that within a predefined longitudinal span a shortest distance between the center points of any two contacts is maximized.

11. A device for deep brain stimulation, comprising:
    a non-bifurcated lead having a longitudinal surface, a proximal end and a distal end; and
    a plurality of electrodes disposed along the longitudinal surface of the lead near the distal end of the lead, the plurality of electrodes comprising at least four segmented electrodes having exposed surfaces, each exposed surface having a center point;
    wherein the center points of the at least four segmented electrodes are disposed on a substantially helical path about the longitudinal surface of the lead wherein all of the segmented electrodes of the device are arranged in either one single helix or one double helix and each electrode is separately activatable.

12. The device of claim 11, wherein the at least four segmented electrodes are disposed in an arrangement that comprises at least one full revolution about the longitudinal surface.

13. The device of claim 11, wherein the at least four segmented electrodes are disposed in an arrangement that comprises two full revolutions about the longitudinal surface.

14. The device of claim 11, wherein the at least four segmented electrodes are configured and arranged so that the center points are uniformly distributed about a portion of the longitudinal surface of the lead.

15. The device of claim 11, wherein the center point of each of the at least four segmented electrodes is equidistant from the center points of the four closest segmented electrodes to that segmented electrode.

16. The device of claim 11, wherein the center points are disposed on the distal end of the lead along a predetermined longitudinal span and arranged about the longitudinal surface of the lead such that the shortest distance between the center points of any two contacts is maximized.

17. An implantable stimulation device, comprising:
    the device of claim 11; and
    a control module coupleable to the lead.

18. The implantable stimulation device of claim 17, wherein the implantable stimulation device is a deep brain stimulator.

19. A method for brain stimulation, the method comprising:
    inserting the device of claim 11 into a cranium of a patient; and
    producing at least one of an anodic current or a cathodic current at the plurality of electrodes to stimulate a target neuron using the plurality of electrodes.

20. The method of claim 19, further comprising modifying a parameter of the anodic and cathodic currents to stimulate a target neural tissue.

* * * * *